United States Patent [19]
Ratkus

[11] Patent Number: 5,149,536
[45] Date of Patent: Sep. 22, 1992

[54] DENTAL ROOT CANAL BACTERIALCIDAL LUBRICANT

[76] Inventor: Victor L. Ratkus, 227 Colchester Ave., Burlington, Vt. 05401

[21] Appl. No.: 804,118

[22] Filed: Dec. 6, 1991

[51] Int. Cl.$^5$ ................................................ B61K 6/00
[52] U.S. Cl. ..................................... 424/401; 514/902
[58] Field of Search ................ 424/401; 514/873, 902

[56] References Cited

U.S. PATENT DOCUMENTS

| | | | |
|---|---|---|---|
| 4,687,663 | 8/1987 | Schaeffer | 514/902 |
| 4,981,686 | 1/1991 | Hardy | 514/873 |

*Primary Examiner*—Thurman K. Page
*Assistant Examiner*—William E. Benston
*Attorney, Agent, or Firm*—Charles J. Prescott

[57] ABSTRACT

A dental root canal bacterialcidal lubricant for allowing the cleaning wires or files to move more freely when removing a nerve from a tooth. The composition also reduces packing of tissue and dental debris within the nerve cavity.

3 Claims, No Drawings

DENTAL ROOT CANAL BACTERIALCIDAL LUBRICANT

BACKGROUND OF THE INVENTION

This invention relates generally to personal and professional health care bacterialcidal lubricants, and more particularly to a bacterialcidal lubricant for use in removing the nerve from the root canal during endodontic therapy.

Thorough cleaning and enlarging of the root canal in conjunction with endodontic therapy has a major impact on the success of such treatment. However, due to the confined work area and the size of the equipment required for this procedure, success is not always assured.

The difficulty and importance of both removing debris and enlarging the root canal or nerve passageway, while also introducing a bacterialcidal component has been described in an article entitled "EDTA and Urea Peroxide for Root Canal Preparation" by G. Stewart in an JADA, VOL. 78, Feb. 1969. Summarizing this article briefly, EDTA (Disodium Ethylenediamine Tetra Acetate) was introduced in 1957 for removing calcium from both dentin and the concretions within the pulp. EDTA permits the reamers and files to clean and enlarge the root canal more readily and has been shown to have antimicrobial activity.

In 1961, Stewart and others introduced urea peroxide in an anhydrous glycerin base as an aid in treating infected root canals. The urea peroxide solution was stable at room temperature, while the glycerin base acted as a lubricant. Another compound, sodium hypochlorite solution reacts with hydrogen peroxide, breaking it down and liberating great quantities of oxygen. In doing so, this combination is useful in floating debris from a root canal, as well as bleaching and deodorizing the tooth. The Stewart article goes on to describe the combination of EDTA and urea peroxide as being an effective aid in cleaning and enlarging root canals. The combination also exhibited good chelating properties, helps float debris from the root canal and altered the surface of the root canal to exhibit complete penetration of medication into the tooth.

Although this treatment is still now utilized in more current endodontic procedures, nonetheless it exhibits limitations of EDTA softening of tooth structure causing ledges or perforations to occur which the present invention overcomes.

The present invention thus provides a more effective lubricant for reducing the friction between the walls of the root canals and the file, while also providing a bacterialcidal effect.

Applicant is also aware of U.S. Pat. No. 4,981,686 to Hardy which teaches a vaginal lubricant having some of the ingredients of the present invention.

BRIEF SUMMARY OF THE INVENTION

This invention is directed to a dental root canal bacterialcidal lubricant for allowing the cleaning wires or files to move more freely when removing a nerve from a tooth. The composition also reduces packing of tissue and dentin debris within the nerve cavity. The compound disclosed by this invention includes cetyl alcohol, sodium lauryl sulfate, propylene glycol, methyl paraben, propyl paraben, butyl, paraben all in a purified water solution.

It is therefore an object of this invention to provide an improved dental root canal bacterialcidal lubricant.

It is yet another object of this invention to provide a dental root canal lubricant which enhances debris removal from the canal zone.

In accordance with these and other objects which will become apparent hereinafter, the instant invention will now be described with reference to the accompanying disclosure.

DETAILED DESCRIPTION OF THE INVENTION

A dental root canal bacterialcidal lubricant in accordance with the present invention includes, in the broad sense, a long straight chain alcohol, a long chain sulfonate salt, a low molecular weight 1, 2 diol, and an alkyl para p-hydroxy benzoate. In a narrower sense, the invention consists essentially of cetyl alcohol, sodium lauryl sulfate, propylene glycol, methyl paraben, propyl paraben, and butyl paraben.

The following examples are provided to illustrate both a typical composition of the invention and the range of ingredients included in the invention.

TABLE I

| Ingredient | Percentage by Weight |
| --- | --- |
| Cetyl alcohol | 4.0% |
| Sodium lauryl sulfate | 1.0% |
| Propylene glycol | 0.5% |
| Methyl paraben | 0.1% |
| Propyl paraben | 0.05% |
| Butyl paraben | 0.02% |
| Purified water | 94.3% |

TABLE II

| Ingredient | Percentage Range by Weight |
| --- | --- |
| Cetyl alcohol | 1.0% to 10.0% |
| Sodium lauryl sulfate | 0.5% to 10.0% |
| Propylene glycol | up to 10.0% |
| Methyl paraben | 0.5% to 2.0% |
| Propyl paraben | 0.025% to 2.0% |
| Butyl paraben | 0.01% to 2.0% |
| Purified water | 64% to 98.4% |

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A dental root canal bacterialcidal lubricant comprising by weight:
    A. cetyl alcohol in the range of about 1% to 10%;
    B. sodium lauryl sulfate in the range of about 0.5% to 10%;
    C. propylene glycol in the range of up to about 10%;
    D. methyl paraben in the range of about 0.5% to 2%;
    E. propyl paraben in the range of about 0.025 to 2%;
    F. butyl paraben in the range of about 0.01 to 2%; and
    G. purified water in the range of about 64% to 98.4%.

2. A dental root canal bacterialcidal lubricant consisting essentially of:
    A. cetyl alcohol;
    B. sodium lauryl sulfate;
    C. propylene glycol;
    D. methyl paraben;

E. propyl paraben; and

F. butyl paraben.

3. A dental root canal bacterialcidal lubricant comprising by weight:

A. cetyl alcohol in the range of 4.0%;

B. sodium lauryl sulfate in the range of 1.0%;

C. propylene glycol in the range of 0.5%;

D. methyl paraben in the range of 0.10%;

E. propyl paraben in the range of 0.05%;

F. butyl paraben in the range of 0.02%; and

G. purified water in the range of 94.3%.

* * * * *